United States Patent [19]

Kondo et al.

[11] Patent Number: 5,071,749
[45] Date of Patent: Dec. 10, 1991

[54] GLYCOPEPTIDE ANTIBIOTIC PA-45052-B

[75] Inventors: Eiji Kondo; Yoshimi Kawamura, both of Osaka; Naoki Tsuji, Hyogo; Koichi Matsumoto, Osaka; Masaaki Kobayashi, Hyogo; Toshiyuki Kamigauchi, Osaka; Yoshiyuki Hayashi, Shiga; Takao Konishi, Osaka, all of Japan

[73] Assignee: Shionogi & Co., Ltd., Osaka, Japan

[21] Appl. No.: 174,449

[22] Filed: Mar. 25, 1988

[30] Foreign Application Priority Data

Apr. 16, 1987 [JP] Japan ................................. 62-94742
Nov. 13, 1987 [JP] Japan ................................ 62-287616

[51] Int. Cl.$^5$ ........................... C07K 7/64; C07K 9/00
[52] U.S. Cl. ................................... 530/317; 530/322; 435/71.3
[58] Field of Search ...................... 514/9, 10; 530/322, 530/317; 435/71, 72, 872, 253.2

[56] References Cited

U.S. PATENT DOCUMENTS 4,122,168 10/1978 Michel et al. .................. 435/72 X
4,548,924 10/1985 Michel ................................ 514/10
4,552,701 11/1985 Nagarajan et al. ............... 530/322
4,558,009 12/1985 Boeck et al. ........................ 435/75
4,843,002 10/1989 Rao et al. ........................ 435/172.3
4,946,941 8/1990 Kondo et al. ..................... 530/317

FOREIGN PATENT DOCUMENTS 201251 12/1986 European Pat. Off. .
0231111 8/1987 European Pat. Off. ............ 530/322

OTHER PUBLICATIONS

Hunt, Ann H. "Structure of the Pseudoaglycon of A35512B." 1983. *Journal of the American Chemical Society* vol. 105, pp. 4463-4468.
Higgens, H. M., et al., 1986, Chemical Abstracts vol. 104, pp. 430-431, No. 49845.
Chemical Abstracts, vol. 110, 1989, 110:33335f.
March, J. 1968, *Advanced Organic Chemistry: Reactions, Mechanisms, and Structure*. McGraw-Hill, New York, pp. 403-404 and 382-387.

*Primary Examiner*—Richard A. Schwartz
*Assistant Examiner*—Mary E. Mosher
*Attorney, Agent, or Firm*—Wenderoth, Lind & Ponack

[57] ABSTRACT

Glycopeptide antibiotics PA-45052 which are produced by *Nocardia orientalis* PA-45052, show potent activity against gram-positive bacteria, especially against methicillin-resistant bacteria, and stimulate growth of animals.

1 Claim, 12 Drawing Sheets

PA-45052-A
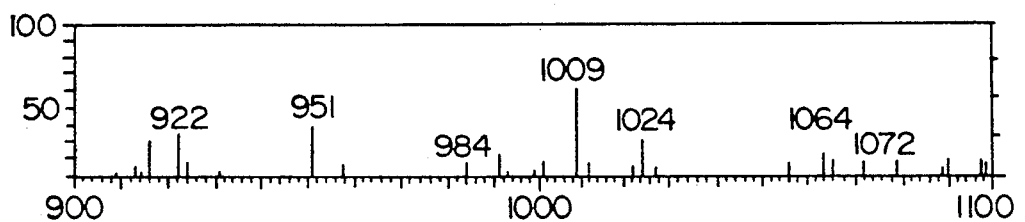
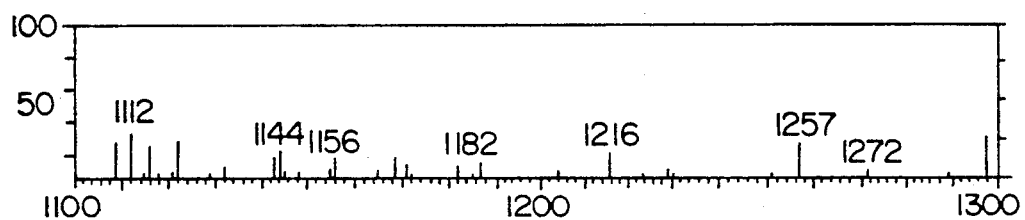
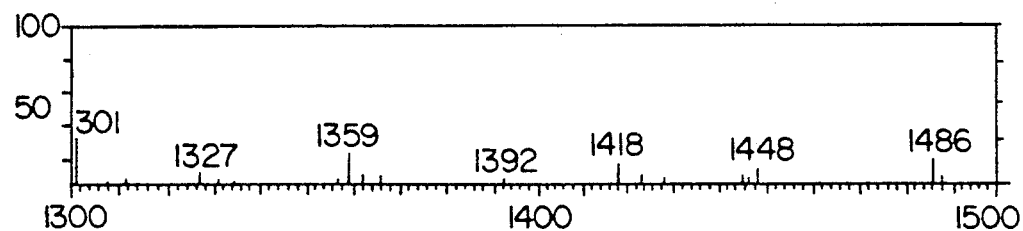
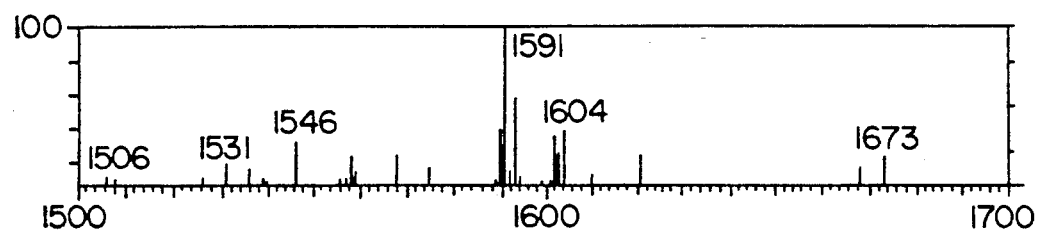
FIG. 2-1

PA-45052-B

PA-45052-C

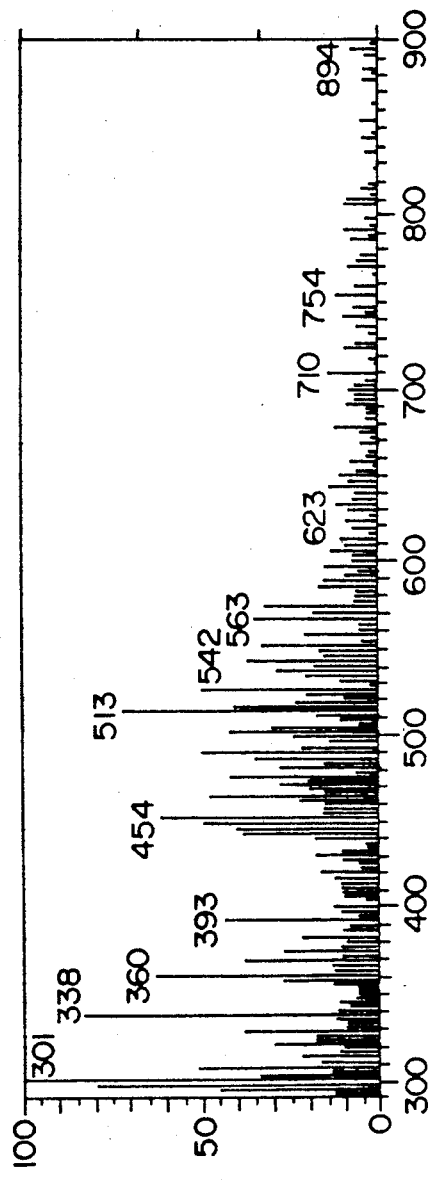
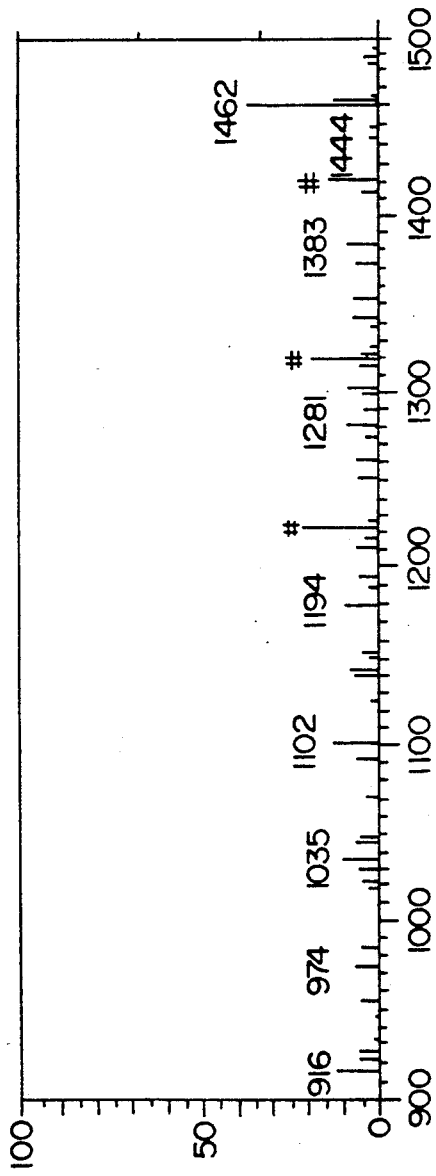
FIG. 2-5

GLYCOPETIDE ANTIBIOTIC PA-45052-B

BACKGROUND OF THE INVENTION

1. Field of the Invention

This invention relates to antibiotics PA-45052 which are represented by the following formula;

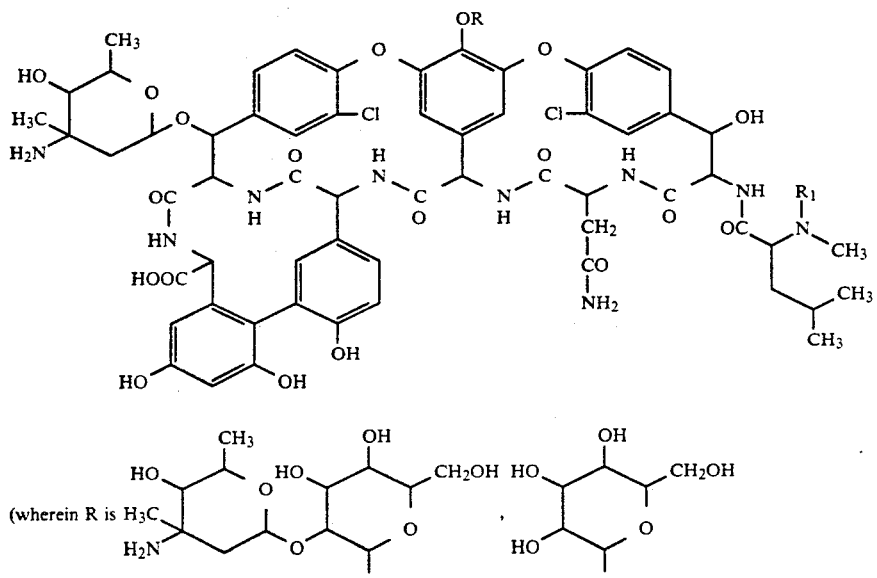

(wherein R is or H and $R_1$ denotes $CH_3$ or $H_1$),
their pharmaceutically acceptable salts, their production, organisms producing them and a growth-stimulating agent containing at least one of them.

2. Prior Art

As antibiotics have recently become to be widely used, the emergence of multiple drug-resistant bacteria, especially methicillin-resistant bacteria provides severe problems. The methicillin-resistant bacteria show resistance not only to methicillin but also to various antibiotics such as aminoglycosides, tetracyclines, cephems, penicillins, carbapenems and macrolides.

It is noticed that glycopeptides, especially vancomycins, show activity against the methicillin-resistant bacteria (Antimicrobial Agent and Chemotherapy, 28, 660–662 (1985)). Vancomycin is a well-known antibiotic (Japanese Patent Publication No. 33-8450) and novel analogs of vancomycin have been discovered (Antimicrobial Agent and Chemotherapy, 28, 660–662 (1985), The Journal of Antibiotics, 37, 446–453 (1984), 38, 1–8 (1985), 38, 51–57 (1985), Japanese Laid-open Patent Nos. 60-139623, 60-199397, 60-231698, 60-237099 etc.). On the other hand, the present inventors found that a strain belonging to the genus Nocardia produces vancomycin antibiotics PA-42867-A and PA-42867-B having a potent antibacterial activity (Japanese Patent Application No. 61-14389) and, in addition, produced its derivatives (Japanese Patent Application No. 61-188865). But the antibiotics PA-45052 of the present invention are vancomycins having completely new structures not coincident to those of the above compounds.

It has been well known that glycopeptide antibiotics such as vancomycins stimulate growth of animals (for example, Japanese Unexamined Patent Publication Nos. 57-129693, 59-213394, 59-213395, 60-199397, 60-231698, 60-237099, 61-122300, 61-251699, 62-126970 and 61-502335; U.S. Pat. Nos. 4,537,770 and 4,558,036; European Patent Publication No. 119575 etc.). However, it has not been known at all that the compounds of this invention have growth-promoting activity. Now, thiopeptin is on the market as growth-stimulating agent.

The problems of infections caused by methicillin-resistant bacteria come to be serious in the clinical field and it is known that glycopeptide antibiotics, especially vancomycin antibiotics have an effectiveness against them. The purpose of this invention is to provide novel vancomycin antibiotics having such an activity as described above and which hence seem to greately contribute to the advancement of medicine.

SUMMARY

This invention provides glycopeptide antibiotics PA-45052-A, -B, -C, -D, -E and -F, which are produced by culturing *Nocardia orientalis* PA-45052, and which show potent activity against gram-positive bacteria, especially methicillin-resistant bacteria, and stimulate growth of animals.

DETAILED DESCRIPTION OF THE INVENTION

The present inventors found that the strain belonging to the genus Nocardia produces compounds which are represented by the following formula:

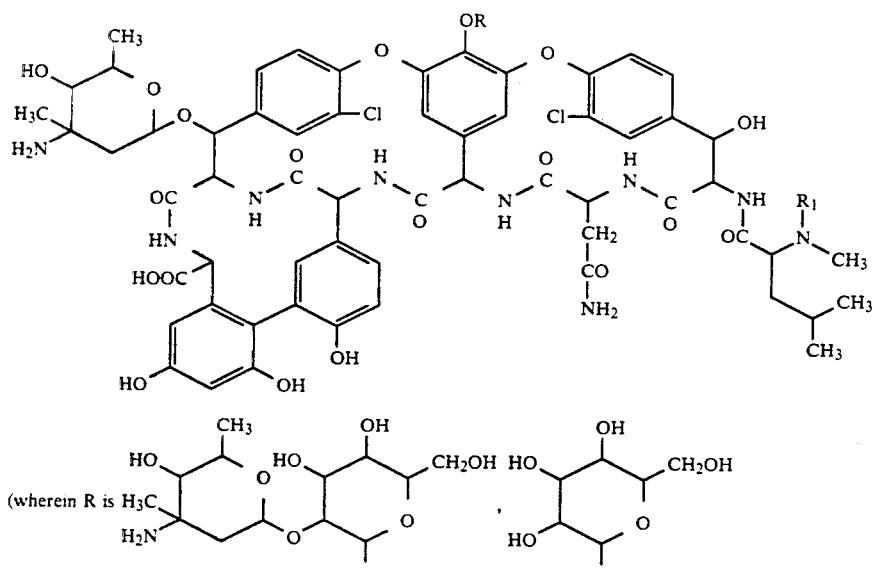

(wherein R is

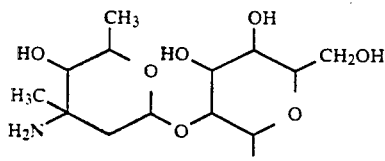

or H and $R_1$ is $CH_3$ or $H_1$)
and which have a strong antibacterial activity, and named a compound of which R in the above formula is

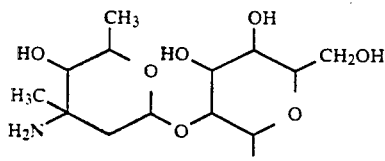

and $R_1$ is H as PA-45052-A, named another compound of which R in the formula is

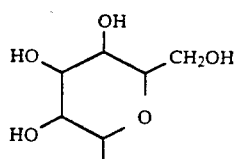

and $R_1$ is H as PA-45052-B, named a further different compound of which R is H and $R_1$ is H as PA-45052-C, named a further different compound of which R is

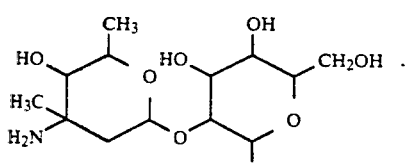

and $R_1$ is $CH_3$ as PA-45052-D, named a further different compound of which R is

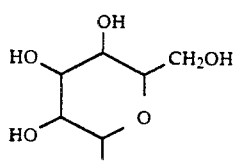

and $R_1$ is $CH_3$ as PA-45052-E, and named a further different compound of which R is H and $R_1$ is $CH_3$ as PA-45052-F. The present invention includes not only these compounds but also their pharmaceutically acceptable salts. PA-45052 described in this specification means mainly any one of the above six compounds but in some cases specifies all of these compounds.

The physicochemical properties of the compounds of this invention are shown below. The appellations PA-45052-A (HCl), PA-45052-B (HCl), PA-45052-C (HCl), PA-45052-D (HCl), and PA-45052-E (HCl) denote that all of them are hydrochlorides.

PHYSICOCHEMICAL PROPERTIES

Ultraviolet Absorption Spectrum

PA-45052-A (HCl): $\lambda_{max}^{0.01 N HCl}$nm ($E_{1cm}^{1\%}$): 281.0 (36.4). $\lambda_{max}^{0.01 N NaOH \cdot aq}$nm ($E_{1cm}^{1\%}$): 301.8 (40.4).

PA-45052-B (HCl): $\lambda_{max}^{0.01 N HCl}$nm ($E_{1cm}^{1\%}$): 281.2 (41.1). $\lambda_{max}^{0.01 N NaOH \cdot aq}$nm ($E_{1cm}^{1\%}$): 302.0 (46.8).

PA-45052-C (HCl): $\lambda_{max}^{0.01 N HCl}$nm ($E_{1cm}^{1\%}$): 279.6 (46.7). $\lambda_{max}^{0.01 N NaOH \cdot aq}$nm ($E_{1cm}^{1\%}$): 296.4 (87.0).

PA-45052-D (HCl): $\lambda_{max}^{0.01 N HCl}$nm ($E_{1cm}^{1\%}$): 280.7 (34.5). $\lambda_{max}^{0.01 N NaOH \cdot aq}$nm ($E_{1cm}^{1\%}$): 301.8 (39.4).

PA-45052-E (HCl): $\lambda_{max}^{0.01 N HCl}$nm ($E_{1cm}^{1\%}$): 280.9 (39.0) $\lambda_{max}^{0.01 N NaOH \cdot aq}$nm ($E_{1cm}^{1\%}$): 302.5 (47.1)

Specific Rotation

PA-45052-A (HCl): $[\alpha]_D^{25°}$: $-87.2 \pm 2.5°$ (c=0.52, water).

PA-45052-B (HCl) $[\alpha]_D^{25°}$: $-67.3 \pm 2.1°$ (c=0.51, water).

PA-45052-C (HCl): $[\alpha]_D^{25°}$: $-59.9 \pm 1.9°$ (c=0.52, water).

PA-45052-D (HCl) $[\alpha]_D^{25°}$: $-86.1 \pm 2.5°$ (c=0.503, water).

PA-45052-E (HCl) $[\alpha]_D^{25°}$: $-71.2 \pm 2.1°$ (c=0.52, water).

Figure 1:
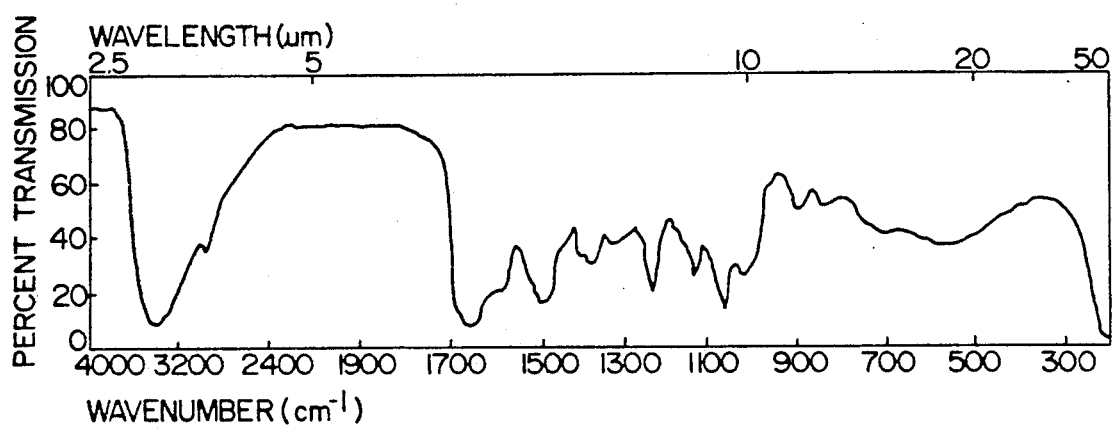
FIG. 1 shows infrared absorption spectra of PA-45052-A, PA-45052-B, PA-45052-C, PA-45052-D and PA-45052-E.
Figure 1:
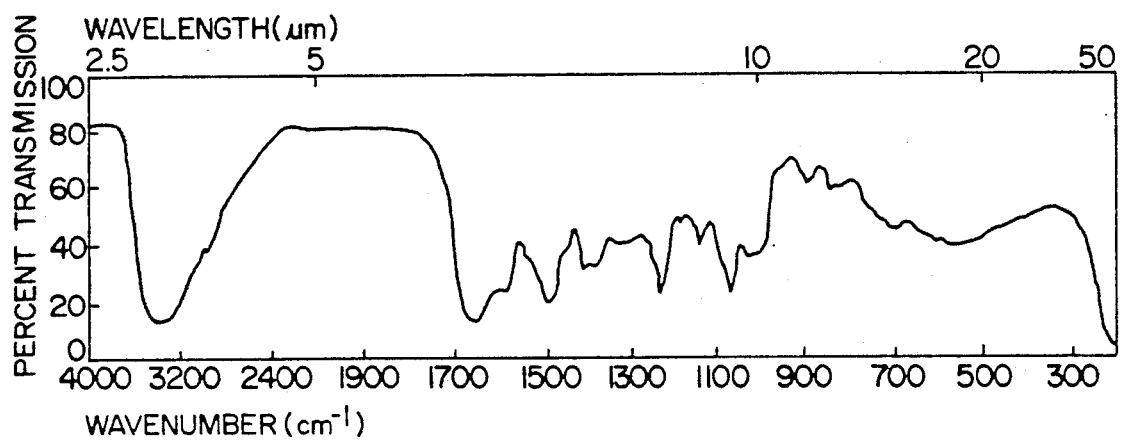
Figure 1:
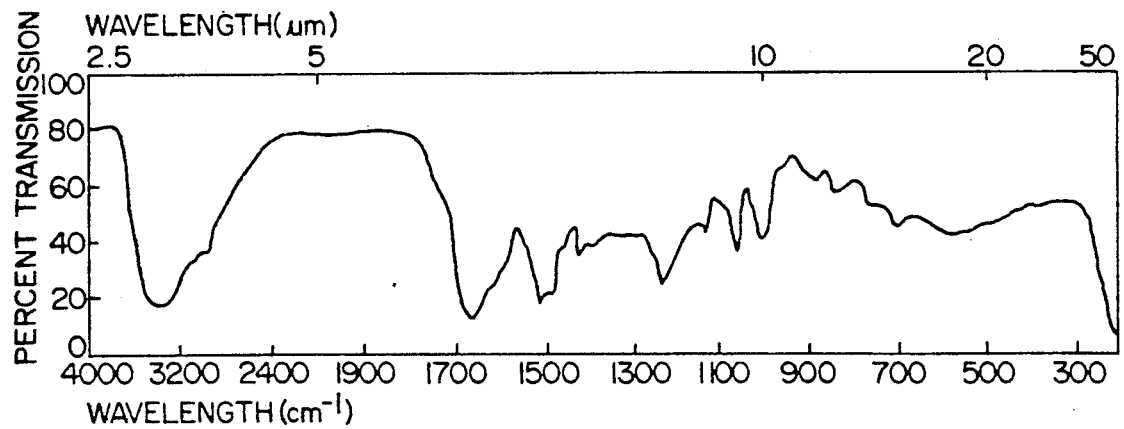

Infrared Absorption Spectrum IR (KBr) $cm^{-1}$ (See FIG. 1)

PA-45052-A (HCl) 3412, 1658, 1589(sh), 1506, 1424, 1397, 1336, 1232, 1133, 1065, 1019, 902. 843.

PA-45052-B (HCl) 3392, 1665, 1589(sh), 1505, 1423, 1400, 1332, 1231, 1132, 1064, 1015, 892, 848.

PA-45052-C (HCl) 3392, 1665, 1624(sh), 1603(sh), 1515, 1501(sh), 1430, 1399, 1233, 1133, 1060, 1002, 889, 848.

PA-45052-D (HCl) 3412, 1655, 1588, 1504, 1420, 1396, 1227, 1130, 1062, 1025, 1014, 998, 900.

PA-45052-E (HCl) 3400, 1654, 1587, 1507, 1489(sh), 1420, 1395, 1228, 1130, 1062, 1026, 1014, 1000.

Figures 1, 2:
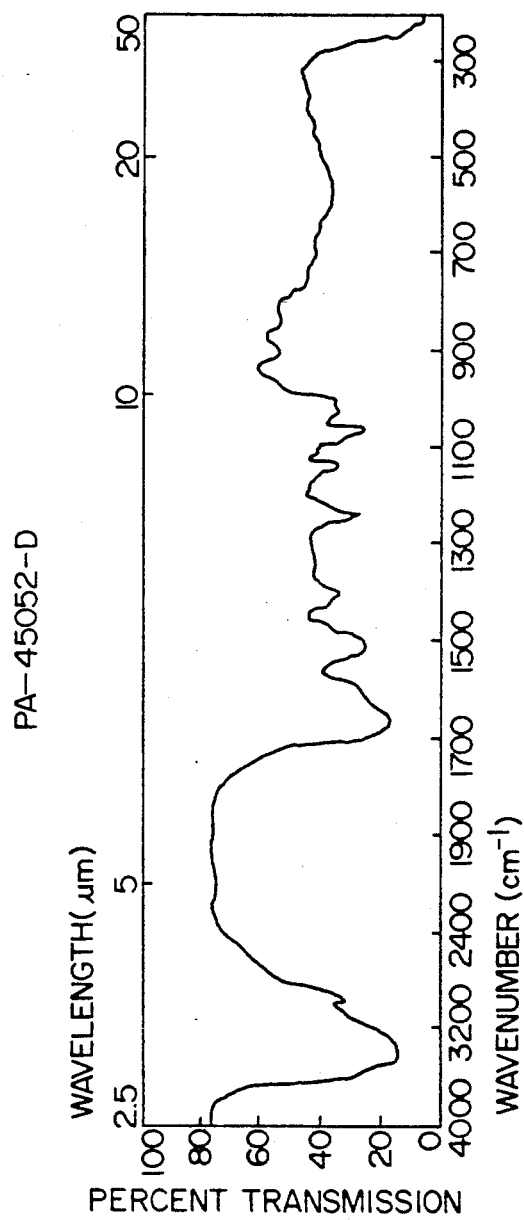
FIG. 2 represents spectra of mass analysis of PA-45052-A, PA-45052-B, PA-45052-C, PA-45052-D and PA-45052-E (peaks marked by # are those of standard substances for marker correction)

Mass Spectrometry (SIMS) (See FIG. 2)

PA-45052-A (Free) 1591 $(M+H)^+$.
PA-45052-B (Free) 1448 $(M+H)^+$.
PA-45052-C (HCl) 1286 $(M+H)^+$.
PA-45052-D (HCl) 1605 $(M+H)^+$.
PA-45052-E (HCl) 1462 $(M+H)^+$.

Elemental Analysis

PA-45052-A (HCl) Anal. Calcd. for $C_{73}H_{88}O_{26}N_{10}Cl_2 \cdot 3/2HCl \cdot 8H_2O$ (%): C: 48.95, H; 5.94, N; 7.82, Cl; 6.93. Found (%): C; 49.01, H; 5.82, N; 7.98, Cl; 7.29.

PA-45052-B (HCl) Anal. Calcd. for $C_{66}H_{75}O_{24}N_9Cl_2 \cdot HCl \cdot 5H_2O$ (%): C; 50.21, H; 5.68, N; 7.98, Cl; 6.74. Found (%): C; 50.38, H; 5.60, N; 8.13, Cl; 6.75.

PA-45052-C (HCl) Anal. Calcd. for $C_{60}H_{65}O_{19}N_9Cl_2 \cdot 2HCl \cdot 6H_2O$ (%): C; 49.09, H; 5.42, N; 8.59, Cl; 9.66. Found (%): C; 49.14, H; 5.49, N; 8.76, Cl; 9.88.

PA-45052-D (HCl) Anal. Calcd. for $C_{74}H_{90}O_{26}N_{10}Cl_2 \cdot 2HCl \cdot 10H_2O$ (%): C; 47.80, H; 6.07, N; 7.53, CL; 7.63. Found (%): C; 47.62, H; 6.00, N; 7.50, Cl; 7.53.

PA-45052-E (HCl) Anal. Calcd. for $C_{67}H_{77}O_{24}N_9Cl_2 \cdot 2HCl \cdot 8H_2O$ (%): C; 47.89, H; 5.70, N; 7.50, Cl; 8.44. Found (%): C; 47.79, H; 5.46, N; 7.80, Cl; 8.47.

Figures 1, 2, 3:
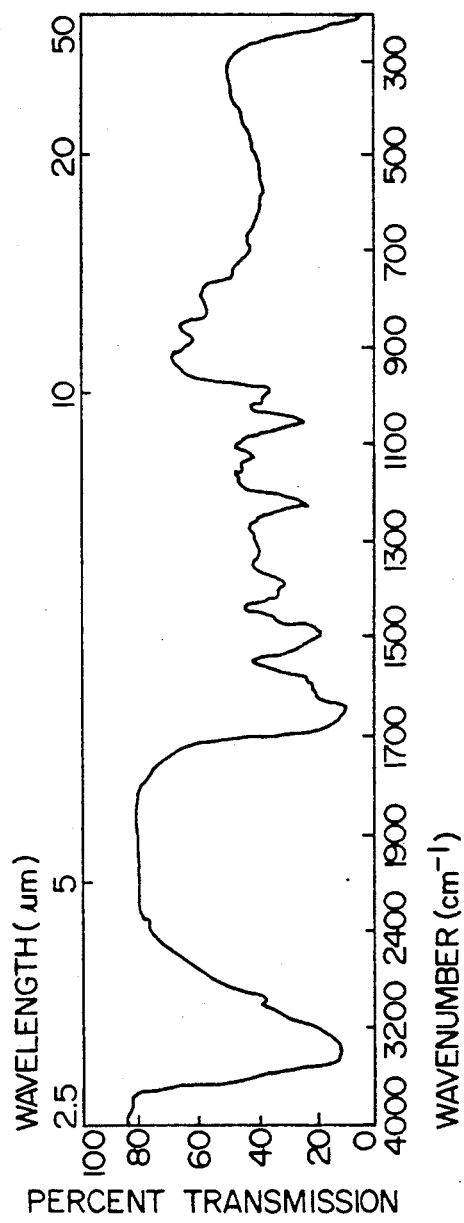
FIG. 3 shows $^1$H-NMR spectra of PA-45052-A, PA-45052-B, PA-45052-C and PA-45052-D.
Figure 2:
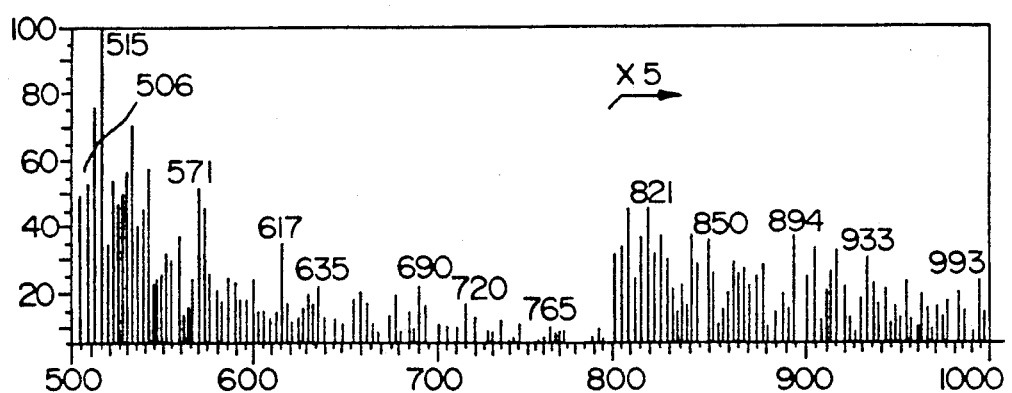
Figure 2:
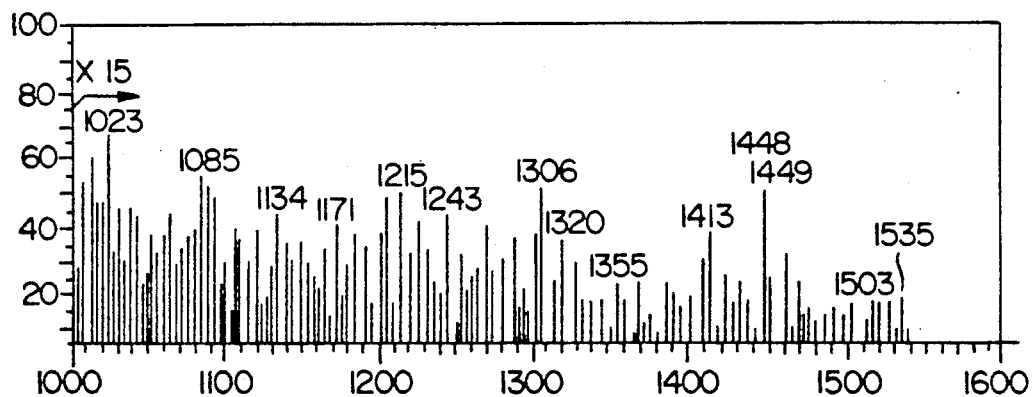
Figure 2:
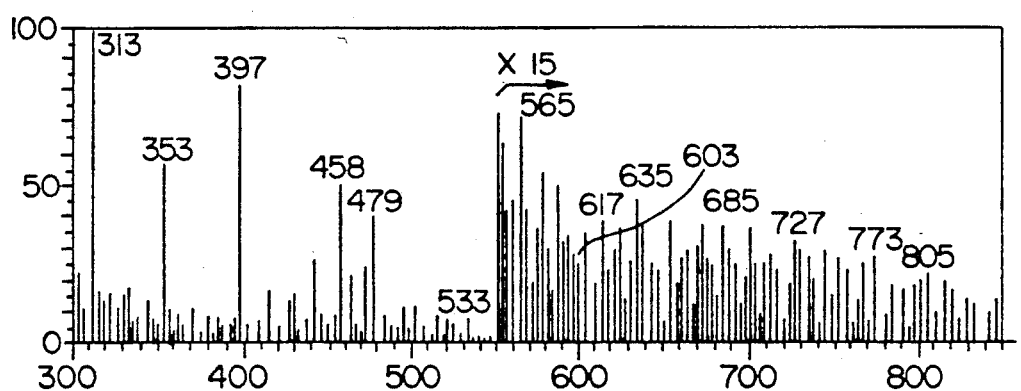
Figure 3:
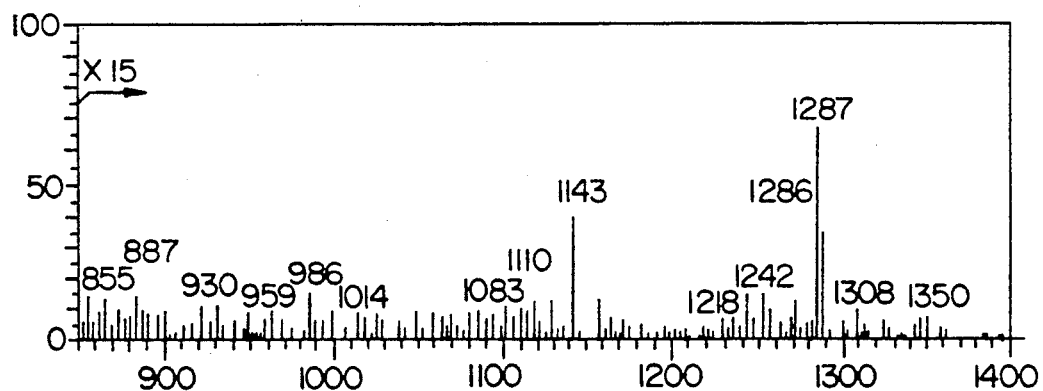
Figures 2, 3, 4:
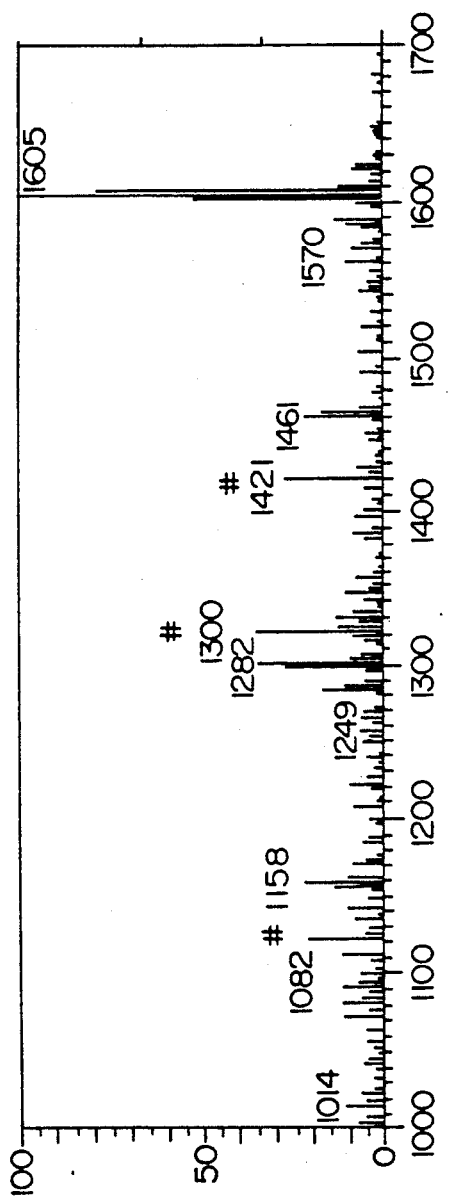
Figures 1, 3:
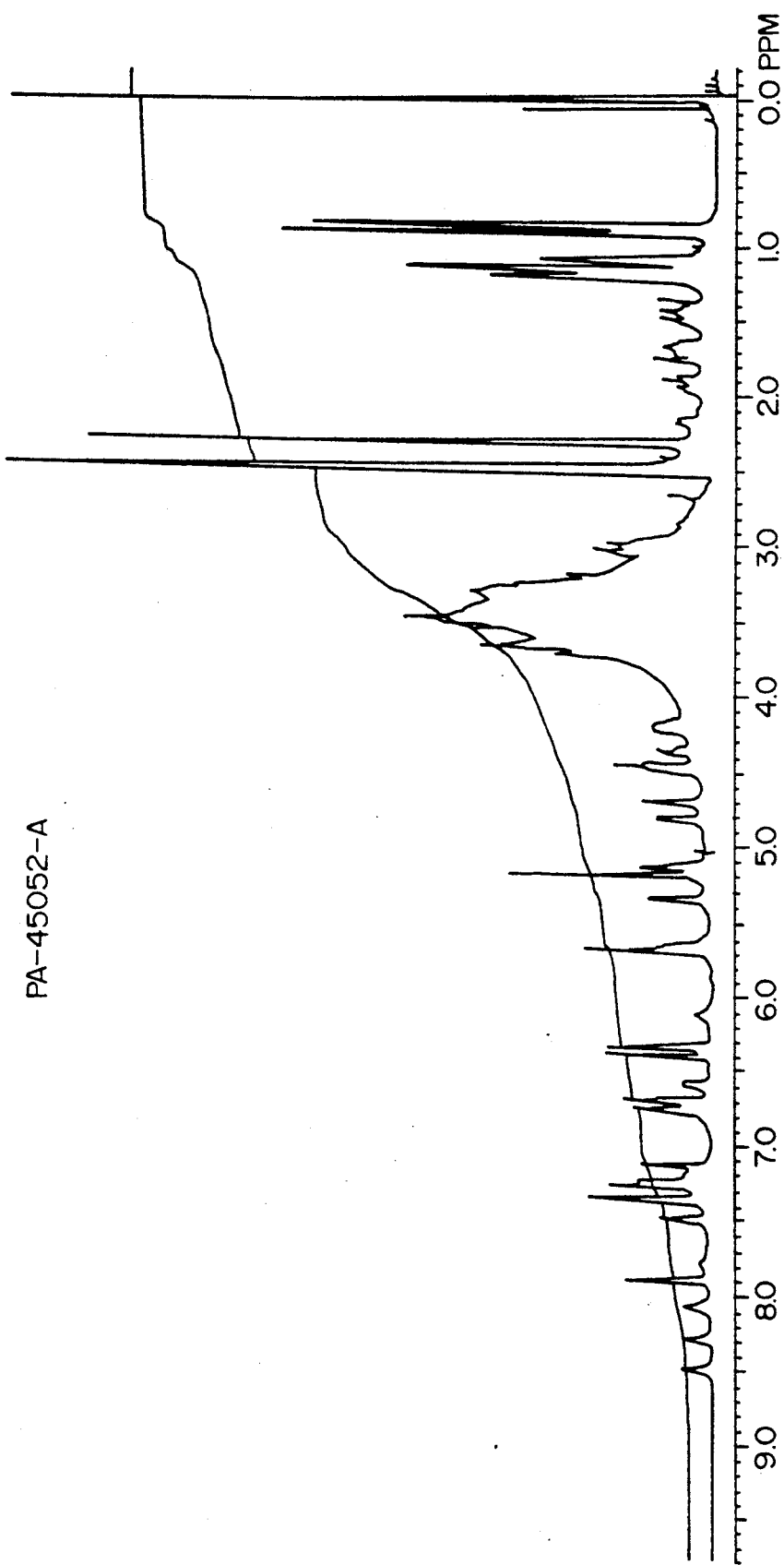
Figures 2, 3:
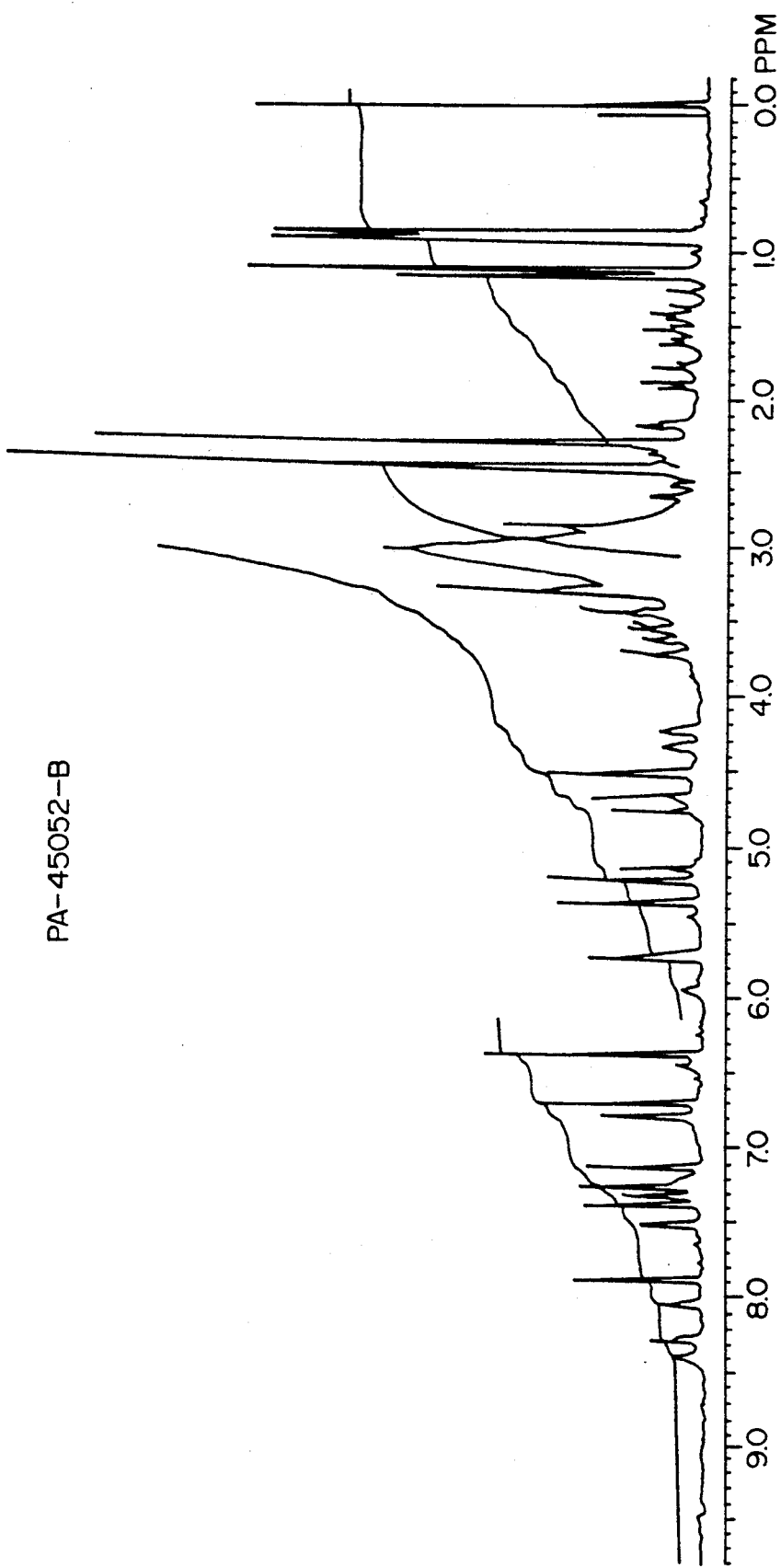
Figure 3:
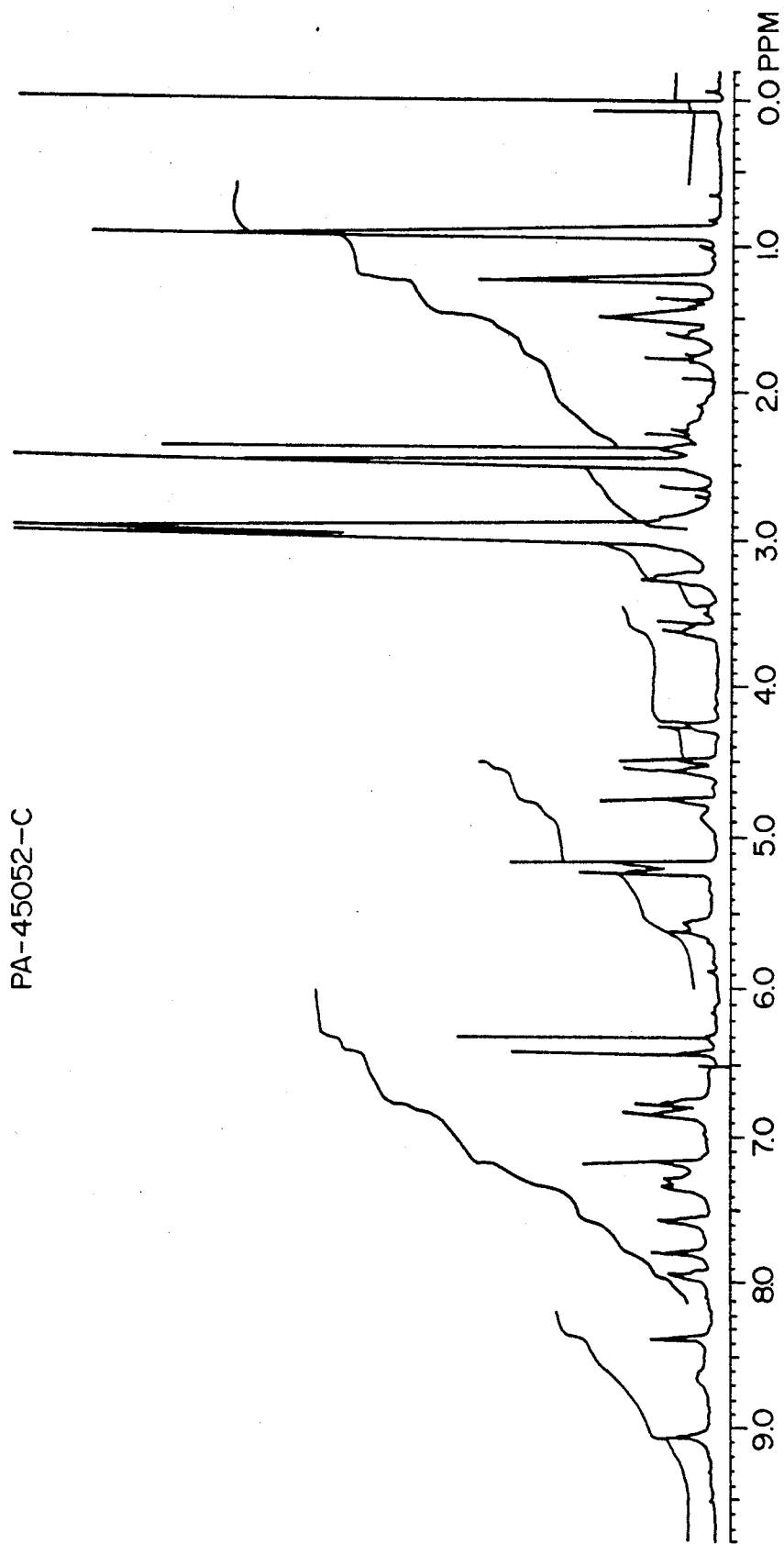
Figures 3, 4:
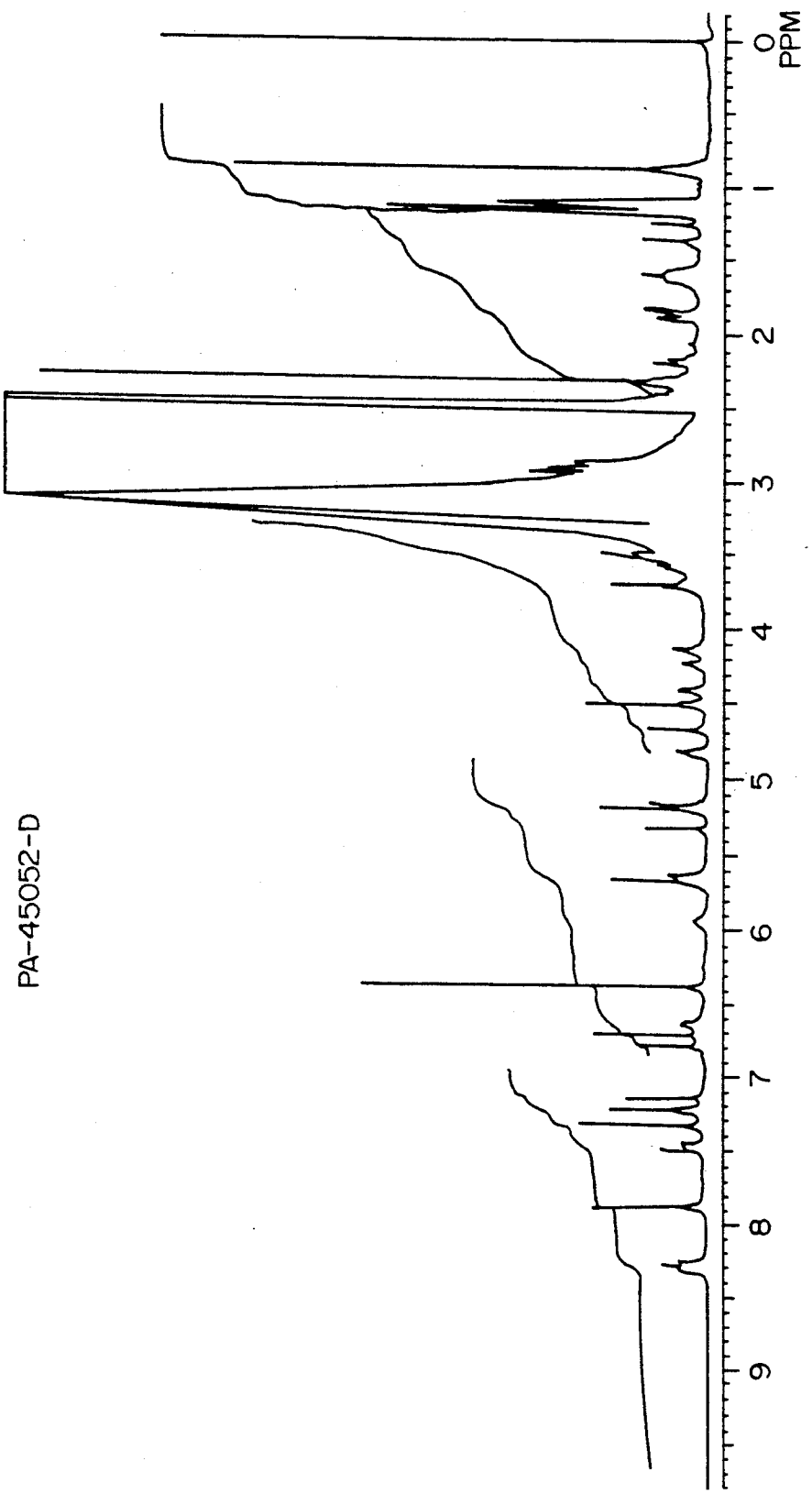

Nuclear Magnetic Resonance Spectrum $^1$H-NMR [400 MHz, $d_6$-DMSO (internal TMS)] {ppm} (See FIG. 3).

PA-45052-A (free) [temp. 60° C.] 8.45 (br-d, -5), 8.29 (d, -6.2), 8.07 (d, 7.5), 7.89 (s-like), 7.78 (br), 7.49 (br-d, -8.5), 7.36 (s-like), 7.36 (br-d, -8), 7.26 (br-d, -8), 7.25 (d, 8.5), 7.14 (s-like), 6.77 (br-d, -8.5), 6.7 (d, 8.5), 6.59 (d, -7), 6.40 (s-like), 6.34 (s-like), 6.13 (br), 5.69 (br-d, -7.5), 5.69 (s-like), 5.65 (d, 7.5), 5.34 (br), 5.19 (s-like), 5.19 (s-like), 5.14 (d, -3.5), 4.81 (br), 4.69 (br), 4.48 (br), 4.45 (d, 6.2), 4.36 (br-m), 4.22 (br), 4.14 (qd, -6, 9.5), 3.74 (br-d), 3.67 (t-like, dd, 7.5, 9), 3.67 (br-m), 3.29 (m), 2.99 (br-d, 9.5), 2.96 (br-d, -9.5), 2.47 (br), 2.31 (s), 2.16 (dd, 16, -7), 1.95 (br-d, 13.5), 1.88 (br-d, -13.5), 1.74 (m), 1.66 (br), 1.65 (br), 1.49 (m), 1.42 (m), 1.21 (s), 1.18 (d, -6), 1.17 (s), 1.09 (d, 6), 0.91 (d, 6.7), 0.87 (d, 6.7)

PA-45052-B (free) [temp. 100° C.] 8.40 (br), 8.29 (d, 6.5), 8.04 (d, 8.5), 7.88 (d, 1.8), 7.52 (dd, 8.4, -2), 7.4 (br-s-like), 7.34 (br-d, 8.4), 7.27 (d, 8.4), 7.23 (br), 7.15 (d, 2.2), 6.80 (dd, 8.4, 2.2), 6.71 (d, 8.4), 6.45 (br), 6.39 (d, 2.2), 6.38 (d, 2.2), 5.96 (br-d, -11), 5.73 (s-like), 5.71 (br-d, -8.5), 5.36 (d, 7.4), 5.23 (s-like), 5.20 (s-like), 5.14 (d, 4.0), 4.76 (d, 4.0), 4.67 (d, 4.2), 4.52 (d, 6.5), 4.50 (d, -6.5), 4.35 (br-m), 4.23 (br-d, -11), 3.71 (d-like, 11.5), 3.62 (q-d, 6.0, 9.7), 3.55 (dd, 11.5, 4.5), 3.44 (t-like), 3.13 (t-like), 3.1 (m), 2.86 (d, 9.7), 2.55 (dd, 16, 7.2), 2.32 (s), 2.17 (dd, 16, 7.2), 1.90 (br-d, 13.5), 1.77 (m), 1.61 (dd, 13.5, 4.2), 1.52 (m), 1.42 (m), 1.17 (d, 6.0), 1.13 (s), 0.92 (d, 6.5), 0.89 (d, 6.5).

PA-45052-C (HCl) [temp. 100° C.] 8.63 (br), 8.37 (d, 5.8), 7.96 (br-d, -8.5), 7.80 (br), 7.59 (br-d, -8.5), 7.36 (br), 7.33 (br), 7.30 (br), 7.19 (br), 7.18 (br-s-like), 6.84 (br-d-like, -8.5), 6.57 (d, -8.5), 6.43 (d, 2.3), 6.33 (d, 2.3), 5.62 (s-like), 5.57 (br), 5.23 (s-like), 5.21 (br), 5.18 (s-like), 4.87 (br), 4.76 (d, 4.0), 4.57 (d, 5.8), 4.50 (d, 5.8), 4.27 (d, 12.0), 3.63 (q-d, 6.1, 9.5), 3.28 (br-d, -9.7), 2.51 (not clear), 2.39 (s), 2.25 (not clear), 1.77 (m), 1.61 (m), 1.49 (m), 1.48 (br), 1.23 (d, 6.1), 0.92 (d, 6.5), 0.90 (d, 6.5).

PA-45052-D (HCl) [temp. 100° C.] 8.312 (br-d, 4.3), 8.283 (d, 6.4), 7.884 (br-d, 9.0), 7.874 (d, 1.5), 7.508 (br-d, 8.8), 7.466 (br-d, 8.8), 7.338 (d, 8.4), 7.327 (br-s), 7.23 (br-d, 8.2), 7.225 (d, 8.4), 7.153 (d, 2.0), 6.795 (d, d, 2.0, 8.4), 6.711 (d, 8.4), 6.646 (br-d, 7.0), 6.375 (s-like), 5.950 (br-d, -10), 5.70 (br-s), 5.667 (d, 7.5), 5.642 (br-d, 8.0), 5.328 (d, 4.5), 5.218 (br-s), 5.193 (br-s), 5.172 (d, 4.0), 4.831 (d, d, 4.0, 9.0), 4.667 (d, 4.2), 4.522 (d, 6.4), 4.506 (d, 6.0), 4.411 (br-m), 4.236 (br-d, 8.2), 4.131 (q, d, 6.8, 9.5), 3.732 (br-d, 10.2), 3.708 (br-t, 8.0), 3.607 (m), 2.913 (br-d, 9.6), 2.865 (br-d, 9.6), 2.419 (d, d, 6.2, 15.9), 2.315 (s), 2.173 (d, d, 6.5, 15.9), 1.886 (br-d, -13.5), 1.863 (br-d, -13.5), 1.38 (m), 1.185 (s), 1.165 (d, 6.5), 1.140 (s), 1.094 (d, 6.0), 0.878 (d, 6.7).

Thin-Layer Chromatography

Merck pre-coated TLC plate silica gel 60F254.

Developing Solvent

Chloroform: methanol: concentrated ammonia water: secondary butanol: water (5:10:5:5:2)

PA-45052-A (HCl) Rf=0.22
PA-45052-B (HCl) Rf=0.22
PA-45052-C (HCl) Rf=0.26

High Performance Liquid Chromatography (HPLC)

Column: Cosmosil 5Ph $\phi$ 4.6×150 mm (Nakarai Chemicals, Ltd.)
Detection: UV 220 nm
Flow rate: 1 ml/min.
Mobile phase: 10% acetonitrile-0.05M phosphate buffer (pH 3.5)
PA-45052-A (HCl)
  Retention time: 4.1 min.
PA-45052-B (HCl)
  Retention time: 9.2 min.
PA-45052-D (HCl)
  Retention time: 6.22 min.
PA-45052-E (HCl)
  Retention time: 13.67 min.
Mobile phase: 17% acetonitrile-0.05M phosphate buffer (pH 3.5).
PA-45052-C (HCl)
  Retention time: 8.8 min.
PA-45052-F (HCl)
  Retention time: 7.93 min.
Column: Nucleosil 5C8 $\phi$ 4.6×150 mm (Chemco)
Detection: UV 220 nm
Flow rate: 1 mililiter/min.
Mobile phase: 10% acetonitrile-0.05M phosphate buffer (pH 3.5)
PA-45052-A (HCl)
  Retention time: 5.6 min.
PA-45052-B (HCl)
  Retention time: 8.8 min.
Mobile phase: 17% acetonitrile-0.05M phosphate buffer (pH 3.5)
PA-45052-C (HCl)
  Retention time: 7.6 min.

Coloration: Positive in ninhydrin reaction
Solubility: Soluble in water and dimethylsulfoxide, slightly soluble in methanol and ethanol and insoluble in ether, benzene, chloroform and ethyl acetate
Properties: Amphoteric matter, white noncrystalline powder From the above physicochemical properties, the compounds PA-45052 of this invention are supposed to have the following steric structures.

Ibaraki-ken, 305 Japan) since Mar. 26, 1987 as *Nocardia orientalis* PA-45052 (FERM BP-1320). Here, the PA-45052 producing organism in this specification means a strain producing at least one compound among PA-45052-A, -B, -C, -D, -E and -F.

Mycological properties of the strain are as follows.

1) Morphological Properties

This strain grows well in yeast malt agar, tyrosine

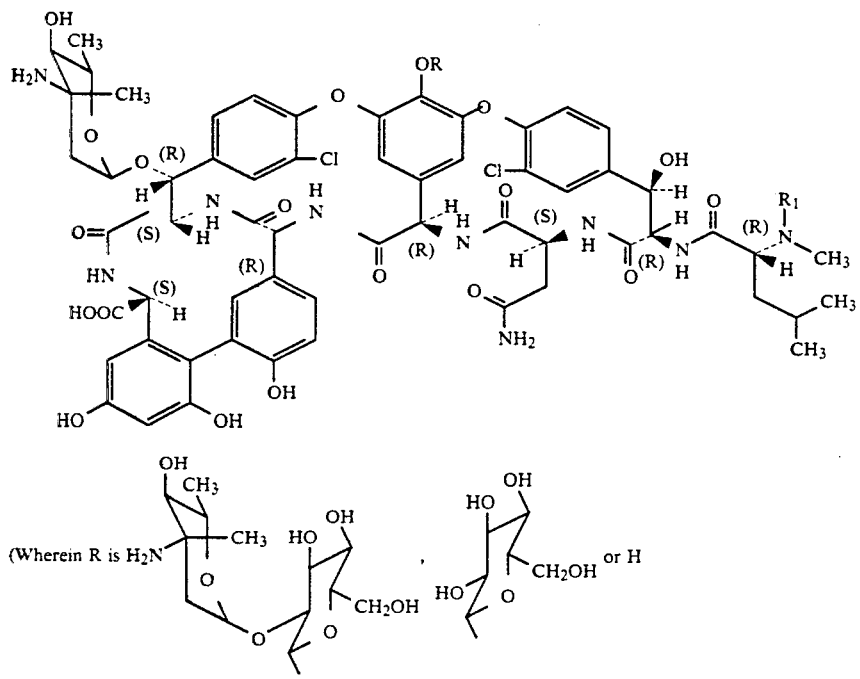

and R₁ is CH₃ or H.)

As described above, compounds PA-45052 have different properties from those of the known glycopeptide antibiotics, so that they are determined to be novel glycopeptide antibiotics.

As one of the PA-45052 producing organisms, PA-45052 strain is exemplified, which is isolated from a soil sample. The strain was identified to be of the same species as *Nocardia orientalis* from a taxonomic consideration, and it has been deposited with Fermentation Research Institute (1-3, Higashi 1 chome Tsukuba-shi agar and Bennett's agar medium and the aerial hyphae adhere to it favorably and the sporulation is satisfactory. The branches are simple without verticillate branch. The aerial hyphae extend relatively long and their tips are straight or wavy. According to the observation under electron microscope, a spore is in an elliptic cylinder form with 0.3 to 0.5 μm in width and 1.2 to 1.8 μm in length, and the surface structure is of smooth type. Neither sporangium, flagellous spore nor sclerotium can be observed.

| | (2) Properties on media (14-day cultivation at 28° C.) | | | | |
|---|---|---|---|---|---|
| | | Aerial hypha | | Color of | Soluble |
| Culture medium | Growth | Formation | Color | Basal hypha | pigment |
| Sucrose nitrate agar medium | Good | Good | White | Pale yellowish brown | None |
| Glucose asparagine agar medium | Good | Good | White | Pale yellowish brown | None |
| Glycerin asparagine agar medium | Good | Good | White | Pale yellowish brown | None |
| Inorganic salt starch agar medium | Good | Fairly good | White | Pale yellowish brown | None |
| Tyrosine agar medium | Good | Good | White | Pale yellowish brown | None |
| Nutrition agar medium | Fairly good | Not formed | — | Pale yellowish brown | None |
| Yeast extract malt extract agar medium | Good | Good | White | Pale yellowish brown | None |

-continued

(2) Properties on media (14-day cultivation at 28° C.)

| Culture medium | Growth | Aerial hypha Formation | Aerial hypha Color | Color of Basal hypha | Soluble pigment |
|---|---|---|---|---|---|
| Oatmeal agar medium | Good | Fairly good | White | Pale yellowish brown | None |
| Bennett's agar medium | Good | Good | White | Pale yellowish brown | None |

Colors conform to "GUIDE TO COLOUR STANDARD" (Japanese Color Institute).

Growth temperature (Cultivated on Bennett's agar medium for 14 days at the following temperatures)
10° C.: Not grown
28° C.: Preferable in growth, formation of aerial hyphae and sporulation
37° C.: Growth was preferable and aerial hyphae were slightly formed.
45° C.: Not grown

(3) Physiological descriptions (28° C., 14-day cultivation)

| | |
|---|---|
| Melanoid chromagenic ability | Negative |
| Tyrosinase reaction | Negative |
| Coagulation of milk | Negative |
| Peptonization of milk | Positive |
| Liquefaction ability of gelatin | Positive |
| Hydrolytic ability of starch | Negative |

4) Usability of Carbon Source

Sugars used well in the growth: L-arabinose, D-xylose, D-glucose, D-fructose, sucrose, inositol, rhamnose, D-mannitol.
Sugars not used in the growth: Raffinose.

5) Composition of Cell Wall

Diaminopimelic acid is of meso form.

From the above properties, the strain is judged to be a strain belonging to the genus Nocardia. Searching for a closely related species to this strain from "The Actinomycetes" (Waxman, vol. 2, 1961), "International Journal of Systematic Bacteriology" [Report of International Streptomyces Project, Shirling and Gottlieb, vol. 18 (1968), vol. 19 (1969), vol. 22 (1972)], Bergey's Manual of Determinative Bacteriology (8th edition, 1974) and other materials related to Actinomyces, it was found that *Nocardia orientalis* (written as *Streptomyces orientalis* in the following materials: International Journal of Systematic Bacteriology vol. 18, pp. 154–157, 1968, The Actinomycetes vol. 2, pp. 254–255, 1961) was the closest species. When comparing the properties of *Nocardia orientalis* with those of PA-45052 strain, most of the principal properties coincided well except for the usability of sucrose. Accordingly, a PA-45052 strain was identified to be the same species as *Nocardia orientalis*, and was named *Nocardia orientalis* PA-45052.

All strains belonging to the genus Nocardia and producing PA-45052-A, -B, -C, -D, -E and/or -F, as well as said PA-45052 strain and its natural or artificial variants, can be used and included in the scope of this invention.

PA-45052 are produced by cultivating PA-45052-producing strain in a nutrient medium under aerobic conditions and recovering PA-45052 from the cultures after the cultivation. General production of PA-45052 is described hereinbelow.

As for components and conditions of the medium, those generally used in the production of antibiotics might be employed. The medium, in principle, contains carbon source, nitrogen source and inorganic salt. Vitamins and precursors might be added as required. As carbon sources, for example, glucose, starch, dextrin, glycerol, molasses and organic acid are used solely or as a mixture. And as for nitrogen sources, for example, soybean powder, corn steep liquor, meat extract, yeast extract, cottonseed powder, peptone, wheat germ, ammonium sulfate and ammonium nitrate are known to be used solely or as a mixture. In addition, the known inorganic salts are, for example, calcium carbonate, sodium chloride, potassium chloride, magnesium sulfate, copper sulfate, manganese chloride, zinc sulfate, cobalt chloride and phosphates, which are added to the medium as required.

The cultivation might be performed by conforming to the method generally used for the production of antibiotics, preferably a liquid culture, and for the purpose of mass production, a submerged aeration culture is suitable. In the case that the pH of the medium might vary, a certain buffer such as calcium carbonate may be added to the medium. The cultivation had better be carried out at about 20° to 40° C.; preferably at 25° to 32° C. The cultivation period depends on the scale of fermentation, and it is 5 to 7 days that are required in mass production. When brisk bubbles are formed during the cultivation, it is better to properly add an antifoam agent such as vegetable oil, lard and polypropylene glycol before or during the cultivation.

In order to recover the PA-45052 from the culture after the cultivation, methods ordinarily used in recovering fermented matter are appropriately used. It is better to properly combine, for example, filtration, centrifugation, adsorption or desorption and chromatography using a variety of ion exchange resins and other activated adsorbents, and extraction by a variety of organic solvents.

For the purpose of isolation or for the convenience of using as medicines for humans or animals, it is sometimes preferable to make PA-45052 salts. The bases capable of forming salts with PA-45052 are alkaline metals such as potassium and sodium, alkaline earth metals such as aluminium and magnesium, while as for acids, inorganic acids such as hydrochloric acid, sulfuric acid, and nitric acid, and organic acids such as acetic acid and fumaric acid are exemplified.

PA-45052 and their pharmaceutically acceptable salts can be administered orally or parenterally to men or animals as active components of antibacterial agent. They can be administered orally as tablets, capsules or powders by using widely employed vehicles, stabilizers, preservatives, humectants and surfactants, and on the other hand, they can be administered parenterally as injections, liniments and suppositories. The dose differs much depending on the purpose of therapy, age of the patient and symptoms, but basically 0.1 to 10 g is preferable a day for an adult by intravenous injection.

The compounds PA-45052 of the present invention show strong antibacterial activity against Gram-positive bacteria; especially methicillin-resistant bacteria and, therefore, are effective as drugs for both men and animals. Besides, as they can be obtained at a high purity, they are suitable to be used as injections as well as oral drugs.

Furthermore, the present inventors found that the compounds PA-45052 have potent activity against the genus Clostridium and animals show remarkable growth when they are fed with a feed to which the PA-45052 is added.

In administering the growth-stimulating agent of this invention, though the glycopeptides of this invention themselves may orally be administered, generally their mixture with usual carriers such as defatted rice bran, defatted bean powder, wheat bran, kaolin, talc, calcium carbonate, lactose, water etc. or a feed or water containing said mixture or the glycopeptides themselves is preferably administered. The glycopeptides used therein need not be pure; for example the partially purified culture of the microorganism of the present invention is applicable. Further, pharmaceutically acceptable salts of the glycopeptides of this invention are also applicable; for example, salts with alkali metal such as potassium and sodium, alkali earth metal such as aluminium and magnesium, inorganic acid such as hydrochloric acid, sulfuric acid and nitric acid and organic acid such as acetic acid and fumaric acid.

The feed which is to contain one or more glycopeptides of this invention may be any one generally used as a feed for animals; for example, the mixture of the whole or a part of corn, wheat bran, rice, wheat, cotton seed cake, milo, soy bean cake, fish powder, defatted rice bran, oil, alfalfa, calcium carbonate, calcium phosphate, sodium chloride, choline chloride, vitamins such as vitamin A, vitamin D, vitamin E, vitamin $B_1$, vitamin $B_2$, vitamin $B_6$, vitamin $B_{12}$, calcium pantothenate, nicotinamide and folic acid and inorganic acids such as magnesium sulfate, iron sulfate, copper sulfate, zinc sulfate, cobalt sulfate and potassium iodide. Other than these, another antibiotic, germicide, anticoccidium and anthelminthic may be added.

The concentration of one or more of the glycopeptides of this invention in a feed may be 0.5 to 100 ppm as a glycopeptide in any case of using one of them alone, a mixture of them, cells containing them or crude extract containing them.

The growth-stimulating agent of this invention may generally be administered to any animals, for example, poultry such as chicken, turkey, duck and quail and cattle such as cow, horse, pig, sheep, goat, mink and rabbit.

In using the growth-stimulating agent of this invention animals may be fed according against to the usual method generally used.

The growth-stimulating agent of this invention not only promotes growth of animals but also improves feed efficiency. Naturally, it is effective against infections by bacteria. Moreover, it has excellent characteristics such that it has little virulence to animals and does not at all accumulate in animals. Values of $LD_{50}$ on injection to mouse regarding the present compounds are shown below.

| | $LD_{50}$ (mg/kg) |
|---|---|
| PA-45052-A | >1000 |
| PA-45052-B | 1439 |

REFERENTIAL EXAMPLE

The PA-45052 of this invention were investigated on the antimicrobial activity against Clostridium perfringens in vitro and the growth-stimulating activity on broiler chicks.

1. In vitro Test on *Clostridium perfringens*

A total of 11 strains of *Cl. perfringens* derived from cow and chicken were used. In measuring the sensitivities, GAM agar medium (Nissui) was used as a medium for assay and anaerobic culture (the gas pack method) was performed according to the agar plate dilution method. The MIC value was determined to be a minimal concentration among the concentrations at which a visual inhibition of the bacteria was clearly observed after incubation at 37° C. for 24 hours.

It has been reported that antibacterial activity against gram positive bacteria, especially *Cl. perfringens* is one of the parameters for growth-stimulating activity of antibiotics in in vitro screening (Poultry Science 62, 1633–1638, 1983; Poultry Science 63, 2036–2042, 1984).

The results are shown below.

| In vitro activity of PA-45052 against *Cl. perfringens* | | | | |
|---|---|---|---|---|
| | | MIC (μg/ml) | | |
| Strain | Origin | PA-45052-A | PA-45052-B | PA-45052-C |
| NCTC-10239 | cow | 0.2 | 0.2 | 0.1 |
| FC 2208/75 | cow | 0.39 | 0.39 | 0.1 |
| S-79 | cow | 0.39 | 0.39 | 0.1 |
| CW-1970 | cow | 0.39 | 0.39 | 0.2 |
| 6B-10 | cow | 0.39 | 0.39 | 0.2 |
| NCTC-8239 | cow | 0.2 | 0.2 | 0.2 |
| NCTC-8798 | cow | 0.39 | 0.39 | 0.2 |
| SP07 | chicken | 0.2 | 0.2 | 0.1 |
| 9C-02 | chicken | 0.39 | 0.39 | 0.2 |
| 3C-01 | chicken | 0.78 | 0.78 | 0.2 |
| 02441 | chicken | 0.39 | 0.39 | 0.2 |

2. Growth-Stimulation Test On Chicks

The growth-stimulating activities of PA-45052-A, PA-45052-B and PA-45052-E on broiler chicks (arbor acre, 8 days old) were investigated by using the known antibiotic thiopeptin as a referential agent. Chicks were fed with a feed mush (crude protein (CP) concentration 18%, each agent's concentration 20 ppm, not supplemented with other antibiotics) for 14 days in the battery brooders. The method of this experiment was as follows. After chicks were fed by floor pen with a feed (CP concentration 23%) from 0 to 8 days, they were divided into 5 groups (24 chicks a group, 12 male and 12 female) in such a way that the average weights of the groups are equal. To each group was administered PA-45052-A (20 ppm), PA-45052-B (20 ppm), PA-45052-E (20 ppm), thiopeptin (20 ppm) or only a feed (CP 18%) for 14 days. Each group was fed in cages (435×600×410 mm, each cage has 6-7 chicks) at 26°±2° C. for 14 days (up to 22 days old). Effectiveness was estimated from the increase of weight and the feed efficiency.

The results are as follows.

| Group | Dose (ppm) | No. of chicks | Increase of weight A (M = g) ± SD | (%) | Feed efficiency B (M = g) | FCR | (%) |
|---|---|---|---|---|---|---|---|
| Control | 0 | 24 | 416.2 ± 60.9 | (100.0) | 713.7 | 1.71 | (100.0) |
| PA-45052-A | 20 | 24 | 440.9 ± 60.4 | (105.9) | 719.1 | 1.63 | (95.3) |
| PA-45052-B | 20 | 24 | 438.5 ± 51.6 | (105.4) | 702.1 | 1.60 | (93.6) |
| PA-45052-C | 20 | 24 | 422.6 ± 61.0 | (101.5) | 678.3 | 1.61 | (94.2) |
| Thiopeptin | 20 | 24 | 431.5 ± 53.4 | (103.7) | 697.1 | 1.62 | (94.7) |

A: average increase of weight
SD: standard deviation
B: average intake of feed
FCR: feed efficiency (B/A)
A value in parentheses is an index when an index of control group is 100.

EXAMPLE

The present invention is detailed in the examples, which, however, are not intended to limit this invention.

(a) Fermentation Process

To a 2-liter Erlenmeyer flask charged with 800 ml of culture medium composed of 0.5% soluble starch, 0.5% glucose, 0.5% polypeptone, 0.5% meat extract, 0.25% yeast extract, 0.25% salt and deionized water (pH 7.0, before sterilization), a seed culture slant of Nocardia orientalis PA-45052 (FERM BP-1320) is inoculated and cultured for 48 hours at 28° C. with shaking at 180 rpm. Each 800 ml of this culture solution is transplanted into a 50-liter jar fermenter charged with 30 liters of culture medium composed of 3.6% dextrin, 2.4% molasses, 0.84% bactopeptone, 0.12% L-tyrosine, 0.05% antifoam P-2000 (produced by Dai Nippon Ink & Chemicals Inc.) and water (pH 7.0, before sterilization), and it is cultured at 32° C. for 137 hours under aeration of 30 liters/min, inner pressure of 0.35 kg/cm$^2$G with stirring at 550 rpm.

(b) Isolation Process

The culture solution obtained in the above process is adjusted to pH 10.5 with 10% sodium hydroxide and 33 liters of supernatant is obtained by centrifugation. After adjusting this supernatant to pH 7.5, it is applied to 3.3 liters of HP-20 column (manufactured by Mitsubishi Chemical Industries, Ltd.). The column is washed with 23 liters of water and then with 10 liters of 15% methanol-0.005N hydrochloric acid and eluted with 50% methanol-0.005N hydrochloric acid. Fractions (9 liters) which show activity in the pulp disk diffusion method using Bacillus subtilis are combined and adjusted to pH 7. The fractions are concentrated in vacuo and freeze-dried to obtain 46.3 g of crude powder of PA-45052.

(c) Purification Process

Preparation of PA-45052-A, -B and -C

Ten grams of said crude powder is suspended in 100 ml of water and dissolved in 1N hydrochloric acid to be adjusted to pH 2.0. The suspension is applied to 100 ml of MCI GEL CHP-20P (produced by Mitsubishi Chemical Industries, Ltd.), which is eluted with 0.01N hydrochloric acid, 10% methanol-0.01N hydrochloric acid, 25% methanol-0.01N hydrochloric acid in this order while checking the content in the fraction by HPLC, and is divided into a fraction containing PA-45052-A and -B and a fraction containing PA-45052-C.

The fraction containing PA-45052-A and -B is adjusted to pH 6.0, concentrated and applied to 100 ml of CHP-20P, which is eluted with water, 30% methanol-water, 50% methanol-water in this order while checking the content by HPLC to obtain a fraction containing PA-45052-A and a fraction containing PA-45052-B. The fraction containing PA-45052-A is adjusted to pH 7.0 and concentrated. After applying to Packed Column RQ-2 (Fujigel Hanbai Co., Ltd.), it is eluted with 13% acetonitrile-0.05M phosphate buffered solution (pH 7.0) (abbreviated to PBS hereinafter) and successively with 15% acetonitrile-0.05M PBS (pH 7.0) while checking the purity by HPLC. And after combining the PA-45052-A fractions (HPLC purity 95% or more), the mixture is concentrated and applied to 12 ml of CHP-20P, which is washed with water and eluted with 50% methanol-water. The resultant is adjusted to pH 4.0, concentrated and freeze-dried to obtain 198 mg of PA-45052-A (HCl).

The fraction containing PA-45052-B is adjusted to pH 7.0, concentrated and applied to Packed Column RQ-2, which is eluted successively with 8% acetonitrile-0.05M PBS (pH 3.5) and 10% acetonitrile-0.05M PBS (pH 3.5) while checking the purity by HPLC. And after combining the PA-45052-B fractions (HPLC purity 95% or more), the mixture is adjusted to pH 7.0, concentrated and applied to 12 ml of CHP-20P, which is washed with water and eluted with 50% methanol-water. As it is colored, the solution is adjusted to pH 7.0 again, concentrated, then adjusted to pH 4.0 and applied to 2 ml of CHP-20P, which is eluted with 0.001N hydrochloric acid to be decolored. Then, fractions of PA-45052-B are collected, adjusted to pH 7.0 and concentrated. The resultant is applied to 12 ml of CHP-20P, which is washed with water and eluted with 50% methanol-water. The resultant is concentrated, adjusted to pH 4.0 and freeze-dried to obtain 290 mg of PA-45052-B (HCl).

The fraction containing PA-45052-C is adjusted to pH 8.5 and adsorbed to 100 ml of CHP-20P, which is washed with water and 50% methanol-water and eluted with 50% methanol-0.01N hydrochloric acid. After combining and concentrating the fractions containing PA-45052-C, the solution is applied to the Packed Column RQ-2, which is successively eluted with 15% acetonitrile-0.05M PBS (pH 3.5) and 18% acetonitrile-0.05M PBS (pH 3.5) while checking the purity by HPLC. And after combining the PA-45052-C fractions (HPLC purity 90% or more), the solution is adjusted to pH 8.0, concentrated and applied to 12 ml of CHP-20P, which is eluted with 18% acetonitrile-0.05M PBS (pH 7.0) successively with 21% acetonitrile-0.05M PBS (pH 7.0) while checking the purity by HPLC. In addition, after combining the fractions of PA-45052-C (HPLC purity 95% or more), the solution is concentrated and applied to 12 ml of CHP-20P, which is washed with water, desalted and successively eluted with 50% methanol-water and 50% methanol-0.01N hydrochloric acid. The eluate is concentrated, adjusted to pH 2.5 and freeze-dried to obtain 365 mg of PA-45052-C (HCl).

Preparation of PA-45052-D

Twenty grams of the crude powder of PA-45052 as described above is suspended in 140 ml of water and dissolved in 1N hydrochloric acid to be adjusted to pH 2.0. This solution is applied to 100 ml of MCI GEL CHP 20P (Mitsubishi Chemical Industries, Ltd.), which is eluted with 0.01N hydrochloric acid while checking the fractions by HPLC. Fractions containing PA-45052-B and -D are adjusted to pH 6.4, concentrated and applied to CHP 20P (100 ml), which is eluted again with 0.01N hydrochloric acid to obtain a fraction containing PA-45052-B and -D. The fraction containing PA-45052-B and -D is adjusted to pH 7.0 and concentrated, then applied to Packed Column RQ-2 (Fujigel Hanbai Co., Ltd.), which is successively eluted with 0.05M PBS (pH 7.0), 13% $CH_3CN$-0.05M PBS (pH 7.0), 15% $CH_3CN$-0.05M PBS (pH 7.0), 18% $CH_3CN$-0.05M PBS (pH 7.0) and 30% $CH_3CN$-0.05M PBS (pH 7.0). From the eluate with 30% $CH_3CN$-0.05M PBS (pH 7.0), a fraction containing PA-45052-D is obtained. The fraction containing PA-45052-D is concentrated and adsorbed to MCI GEL CHP 20P (10 ml), which is washed with water and successively eluted with 25% $CH_3OH$-$H_2O$ and 50% $CH_3OH$-$H_2O$. Desalted fractions are combined and concentrated. After being adjusted to pH 4.0 with hydrochloric acid, it is freeze-dried to obtain PA-45052-D (665 mg, hydrochloride salt) as white noncrystalline powder.

Preparation of PA-45052-E

Twenty grams of the crude powder of PA-45052 as described above is suspended in 140 ml of water and dissolved in 1N hydrochloric acid to be adjusted to pH 2.0. This solution is applied to 100 ml of MCI GEL CHP 20P (Mitsubishi Chemical Industries, Ltd.), which is eluted with 0.01N hydrochloric acid, 10% methanol-0.01N hydrochloric acid and 25% methanol-0.01N hydrochloric acid in this order. By checking the fractions by HPLC, a fraction containing PA-45052-A, -B, -D and -E and a fraction containing PA-45052-C and -F are obtained. The fraction containing PA-45052-A, -B, -D and -E is adjusted to pH 6.4 and concentrated, then applied to CHP 20P (100 ml), which is eluted again with 0.01N hydrochloric acid to obtain a fraction containing PA-45052-A and a fraction containing -B, -D and -E. The fraction containing -B, -D and -E is adjusted to pH 7.0, concentrated and applied to Packed Column RQ-2 (Fujigel Hanbai Co., Ltd.), which is successively eluted with 0.05M PBS (pH 7.0), 13% $CH_3CN$-0.05M PBS (pH 7.0), 15% $CH_3CN$- 0.05M PBS (pH 7.0), 18% $CH_3CN$-0.05M PBS (pH 7.0) and 30% $CH_3CN$- 0.05M PBS (pH 7.0). From the eluate with 30% $CH_3CN$-0.05M PBS (pH 7.0), a fraction containing -D and a fraction containing -E are obtained. The fraction containing PA-45052-E is concentrated and adsorbed to MCI GEL CHP 20P (10 ml). After being washed with water, it is eluted with 25% $CH_3OH$-$H_2O$ and 50% $CH_3OH$-$H_2O$ in this order. The fractions containing -E are then combined and concentrated. After being adjusted to pH 4.0 with hydrochloric acid, it is freeze-dried to obtain PA-45052-E (245 mg, hydrochloride salt) as white noncrystalline powder.

Preparation of PA-45052-F

The fraction containing PA-45052-C and -F is adjusted to pH 8.0 and adsorbed to CHP 20P (100 ml). After being washed with water and 50% methanol solution, it is eluted with 50% methanol-0.01N hydrochloric acid. Fractions containing PA-45052-C and -F are concentrated and applied to Packed Column RQ-2, which is eluted with 15% $CH_3CN$-0.05M PBS (pH 3.5) and 18% $CH_3CN$-0.05M PBS (pH 3.5) to obtain a fraction containing PA-45052-C and -F. The fraction containing PA-45052-C and -F is adjusted to pH 8.0 and concentrated, and sequentially applied to CHP 20P (10 ml), which is eluted with 18% $CH_3CN$-0.05M PBS (pH 7.0), 21% $CH_3CN$-0.05M PBS (pH 7.0), 30% $CH_3CN$-0.05M PBS (pH 7.0) and 50% $CH_3CN$-0.01N hydrochloric acid in this order to obtain a fraction containing PA-45052-C and a fraction containing PA-45052-F. The fraction containing PA-45052-F is concentrated and adsorbed to CHP 20P (10 ml), which is washed with water to be desalted and then eluted with 50% methanol solution and 50% methanol-0.01N hydrochloric acid. After being concentrated, it is adjusted to pH 2.5 and freeze-dried to obtain 30 mg of PA-45052-F (hydrochloride salt).

EXAMPLE 2

(a) Fermentation Process

To a 2-liter Erlenmeyer flask charged with 800 ml of culture medium composed of 0.5% soluble starch, 0.5% glucose, 0.5% polypeptone, 0.5% meat extract, 0.25% yeast extract, 0.25% salt and deionized water (pH 7.0, before sterilization), a seed culture slant of *Nocardia orientalis* PA-45052 (FERM BP-1320) is inoculated and cultured for 48 hours at 28° C. with shaking at 180 rpm. This culture solution (800 ml) is transplanted to a 30-liter jar fermenter charged with 18 liters of culture medium composed of the same ingredients as the above and cultured under the conditions of 18 liters/min of aeration, 0.35 kg/cm²G of inner pressure, 200 rpm of stirring speed, at 32° C. for 23 hours. Then, 8 liters of this culture is transplanted to a 250-liter fermentation tank charged with 165 liters of a culture medium composed of 2.0% potatostarch, 1.0% glucose, 3.0% molasses, 1.1% bactopeptone, 0.05% antifoam P-2000 (manufactured by Dai Nippon Ink and Chemicals) and water (pH 7.0 before sterilization) and is cultured at an aeration of 165 liters/min, inner pressure of 5 psi, at stirring speed of 350 rpm at 32° C. for 164 hours.

(b) Isolation Process

The culture solution obtained in the above process is adjusted to pH 10.5 with 10% sodium hydroxide and 140 liters of the supernatant is obtained by centrifugation. After adjusting this supernatant to pH 7.5, it is applied to a 15 liters of HP-20 column (produced by Mitsubishi Chemical Industries). Then, after washing with 23 liters of water and then with 30 liters of 15% methanol-0.005N hydrochloric acid, it is eluted with 50% methanol-0.005N hydrochloric acid. Then 53 liters of fractions showing the activity by the pulp disk diffusion method using *Bacillus subtilis* are collected and adjusted to pH 7. Finally, this mixture is concentrated in vacuum and freeze-dried to obtain 150.8 g of crude powder of PA-45052.

6) Effects of the Invention

In vitro antibacterial activity was determined by the agar dilution method as described below.

① Preparation of Bacterial Suspension

One loopful of each test bacterium on a slant was inoculated into 1 ml of a growth medium (Trypto Soy Broth, Eiken Chemical Co.) and incubated at 37° C. for 18-20 hours. For the growth of Streptococci, Mueller-Hinton broth (Difco) supplemented with 3% (V/V) horse serum was employed. A hundred-fold dilution of the culture is used as an inoculum suspension of the bacterium.

② Sample Solution

The sample (9-10 mg) was weighed and dissolved in distilled water at a concentration of 2 mg/ml.

③ Agar Plate

A sample solution was subjected to serial two fold dilution with sterile water (2000-0.25 μg/ml). To sterile plastic petri dishes (9 cm in diameter) was poured 0.5 ml-aliquot of sample solutions, which was mixed with 9.5 ml of an agar medium (Sensitivity Test Agar, "Nissui"). For Streptococci, horse serum was supplied at 0.5% (V/V).

④ Measurement of MIC Value

One loopful (1.0 μl) of the inoculum suspension was placed on the surface of the agar plates prepared as noted above. The bacterial growth was examined visually after overnight incubation (18-20 hrs) at 37° C. The lowest concentration, at which bacterial growth is completely inhibited, is determined to be MIC (minimal inhibitory concentration).

The results are shown in Table 1.

EXAMPLE 3

An addition of each compound as a growth-stimulating agent of this invention is exemplified below.

(1)
| | |
|---|---|
| corn | 46.45% |
| milo | 15.00% |
| soy bean cake | 5.00% |
| fish powder | 3.00% |
| defatted rice bran | 25.00% |
| alfalfa | 3.00% |
| calcium carbonate | 1.00% |
| calcium phosphate | 0.70% |
| sodium chloride | 0.40% |
| mixture of vitamins A, D and E | 0.05% |
| mixture of inorganic salts | 0.1% |
| mixture of vitamins B | 0.1% |
| PA-45052-A | 10 ppm |

*mixture of inorganic salts: manganese sulfate, zinc sulfate, copper sulfate, cobalt sulfate and potassium iodide
**mixture of vitamins B: vitamins $B_1$, $B_2$, $B_6$ and $B_{12}$, biotin, folic acid and calcium pantothenate (2)
| | |
|---|---|
| corn | 41.00% |
| milo | 25.00% |
| soy bean cake | 19.10% |
| fish powder | 8.00% |
| oil | 4.00% |
| calcium carbonate | 1.40% |
| calcium phosphate | 0.85% |
| *mixture of vitamins and inorganic salts | 0.26% |
| methionine | 0.10% |
| sodium chloride | 0.29% |
| PA-45052-B | 20 ppm |

*mixture of vitamins and inorganic salts: vitamins A, $D_3$, E, $B_1$, $B_2$, $B_6$, $B_{12}$ and $K_4$, calcium pantothenate, nicotinamide, choline chloride, magnesium sulfate, iron sulfate, copper sulfate, zinc sulfate, cobalt sulfate and potassium iodide (3)
| | |
|---|---|
| corn | 78% |
| soy bean cake | 9% |
| fish powder | 10% |

TABLE 1

| Test organism | MIC (μg/ml) | | | | |
|---|---|---|---|---|---|
| | PA-45052-A | PA-45052-B | PA-45052-C | PA-45052-D | PA-45052-E |
| *Staphylococcus aureus* PDA 209P JC-1 | 0.2 | 0.39 | 0.2 | 0.2 | 0.39 |
| *Staphylococcus aureus* SMITH | 0.39 | 0.78 | 0.39 | 0.39 | 0.78 |
| *Staphylococcus aureus* ATCC 25923 | 0.39 | 0.39 | 0.39 | 0.78 | 0.78 |
| *Staphylococcus aureus* SR14** | 0.39 | 0.78 | 0.39 | 0.39 | 0.78 |
| *Staphylococcus aureus* SR3131* | 0.39 | 0.39 | 0.39 | 0.39 | 0.78 |
| *Staphylococcus aureus* SR1626* | 0.39 | 0.78 | 0.39 | 0.39 | 0.78 |
| *Staphylococcus aureus* SR3626* | 0.39 | 0.39 | 0.39 | 0.78 | 0.78 |
| *Streptococcus epidermidis* ATCC 14490 | 0.78 | 1.56 | 0.78 | 0.78 | 3.13 |
| *Streptococcus pyogenes* C-203 | 0.2 | 0.2 | 0.2 | 0.2 | 0.39 |
| *Streptococcus pneumoniae* Type I | 0.1 | 0.2 | 0.2 | 0.2 | 0.39 |
| *Streptococcus agalactiae* SR 1247 | 0.2 | 0.39 | 0.2 | 0.2 | 0.39 |
| *Streptococcus faecalis* SR 1004 | 0.78 | 0.78 | 0.39 | 0.78 | 1.56 |

*Methicillin-resistant bacteria
**Penicillin-resistant bacteria

The antibacterial activity of PA-45052-A, -B and -C in vivo is next shown in Table 2.

Test method: The test organism is intraperitoneally inoculated to Slc-ICR female mice (8 mice per group), and PA-45052-A, -B or -C (two-fold dilution) is subcutaneously administered twice one hour later and 5 hours later.

Results: The 50% effective dose ($ED_{50}$) is calculated from the survival rate on day 7.

| | |
|---|---|
| oil | 3.9% |
| crude fiber | 2.4% |
| crude ash | 5.1% |
| calciam | 1.07% |
| phosphate | 0.73% |
| mixtnre of alfalfa meal, sodium chloride and calcium carbonate | 3% |
| PA-45052-B | 20 ppm |

(4) One or more of PA-45052 are mixed in a similar way to the above to prepare an agent-

TABLE 2

| Test organism | $ED_{50}$ (mg/kg/dose) | | |
|---|---|---|---|
| | PA-45052-A | PA-45052-B | PA-45052-C |
| *Staphylococcus aureus* SR 3637* | 1.91 | 2.84 | 3.39 |
| *Staphylococcus aureus* SR 2030* | 0.99 | 1.45 | 1.91 |
| *Streptococcus pneumoniae* Type I | 0.19 | 0.38 | 0.29 |
| *Streptococcus pyogenes* C-203 | 0.14 | 0.44 | 0.35 |

*Methicillin-resistant bacteria

What is claimed is:
1. A compound PA-45052-B represented by the formula;
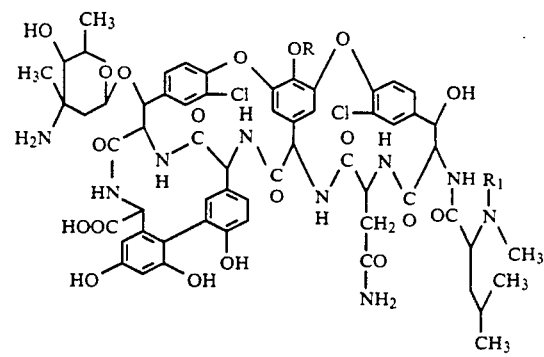
and $R_1$ is H,
or its pharmaceutically acceptable salt.